United States Patent
Sarango

(12) 
(10) Patent No.: US 6,540,702 B1
(45) Date of Patent: Apr. 1, 2003

(54) BREAST COMPRESSING DEVICE

(76) Inventor: Maria Sarango, 76 Vista Montemar, Laguna Nigal, CA (US) 92677

( * ) Notice: Subject to any disclaimer, the term of this patent is extended or adjusted under 35 U.S.C. 154(b) by 207 days.

(21) Appl. No.: 09/703,606

(22) Filed: Nov. 1, 2000

(51) Int. Cl.[7] ............................. A61B 17/08; A41C 3/10
(52) U.S. Cl. ....................... 601/133; 601/134; 606/201; 450/45; 450/54
(58) Field of Search ..................... 604/74, 514; 601/14, 601/148, 149, 150, 151, 152, 133, 134; 606/201, 204; 602/19; 450/18, 38, 45, 52, 53, 55; 623/7

(56) References Cited

U.S. PATENT DOCUMENTS

| | | | |
|---|---|---|---|
| 990,279 A | * | 4/1911 | Mayer et al. |
| 2,598,003 A | * | 5/1952 | Leo et al. |
| 3,326,218 A | * | 6/1967 | McAlpine |
| 4,205,681 A | * | 6/1980 | Nestor et al. ................ 606/151 |
| 6,015,332 A | * | 1/2000 | Lee et al. ...................... 450/38 |

* cited by examiner

Primary Examiner—Danton D. DeMille
(74) Attorney, Agent, or Firm—Michael I. Kroll

(57) ABSTRACT

A device for compressing a breast. The device includes a harness able to be releasably secured to a body of a user and a compression member adjustably connected to the harness for receiving the breast of the user. A control module is releasably secured to the harness for providing a pressure to the compression member for applying an equal compression force to the breast. The compression member includes a first compressing element positioned on a first side of the breast; a second compression element positioned on a second side of the breast opposite the first compressing element; and a structural member extending between the first and second compressing elements for retaining the first and second compressing elements on respective sides of the breast whereby an aperture defined by the structural member and first and second compressing elements for receiving the breast therein. The harness includes a first strap for securing the device about a waist of the user and a shoulder strap adjustably connected to the first strap for retaining the compression member aligned with the breast of the user. The structural member includes a first length adjustable structural element extending between a first end of both the first and second compressing elements and a second length adjustable structural member extending between a second end of both the first and second compressing elements. The control element includes a pump and supply line connected between the pump and both the first and second compressing elements for providing air pressure thereto.

12 Claims, 9 Drawing Sheets

BREAST COMPRESSING DEVICE

BACKGROUND OF THE INVENTION

1. Field of the Invention

The present invention relates generally to devices for compressing the breasts of a woman and, more specifically, to a device which is able to support a breast of a woman and provide a compression force in a controlled even manner on either side of the breast for relieving the effects of Capsular Contracture.

The function of the present invention is to provide patients after breast reconstruction following mastectomy or breast augmentation, an in-house device to prevent capsular contracture. The Breast Compression Device will be increasing breast implants surface area during the compression cycles by changing the shape of the implant from a substantially spherical to elliptical shape and thereby stretching the periprosthetic contracting scar. While the use of this device will vary according to the individual the normal application will consist of a number or repetitions of 10 seconds of pressurization and 10 seconds of rest.

2. Description of the Prior Art

Capsular Contracture is a common complication following such surgeries. When tissue is injured, the body tries to repair the defect by generating new blood vessels at the periphery of the injury by secreting collagen to form a new tissue matrix. Often the blood vessels regress leaving excess collagen to form scar tissue. After breast augmentation and breast reconstruction surgeries, excess collagen scar tissue result in spherical Capsular Contracture that surrounds the breast implant causing significant discomfort, pain, distortion and displacement of the implant.

There are three basic treatments for Capsular Contracture. In the technique known as Closed Capsulotomy, the doctor squeezes the hardened tissue in order to break it. Implant manufacturers do not recommend this procedure because this abnormal and uncontrolled force can result in hemorrhaging and can rupture the implant. In Open Capsulotomy, the doctor surgically breaks up the scar tissue. In Capsulotomy, the scar tissue is surgically removed. With all three treatments, even if Capsular Contracture is relieved, it might recur,- warning Dow Coming, Implant Information Booklet.

Many doctors recommend continuous manual self-compression of the breast for several months after surgery in order to prevent Capsular Contracture. The disadvantage of manual compression is the force that the patient is capable of producing is not linear safety and effectiveness.

Numerous types of devices for compressing and supporting a breast of a woman have been provided in the prior art. For example, U.S. Pat. Nos. 4,202,343; 5,050,595;5,823, 851;5,891,070;5,904,607;5,950,238; 5,968,003 and 6,022, 317 all are illustrative of such art.

A brassiere comprising a body encircling band having a pair of breast cups and shoulder straps, and a pair of midriff straps secured at the bottom of the breast cups to a waist encircling garment such as a belt or shorts, the midriff straps being used to urge the breast downwardly to prevent undo movement thereof while jogging. In an alternate brassier, the shoulder straps cross at the wearers back, pass through loops at the side and extend upwardly to where they are secured to the lower portion of the breast cups, the loops being secured to the waist encircling garment.

A women therapeutic support garment comprising a pair of breast supporting cups each of which is formed with an inner and outer panel defining therebetween one of two cupped shaped pockets. A cup shape, thermal gel pack is placed in each pocket and has a central opening for accommodation the women nipple. A pair of side panels are connected to the breast supporting cups, the side panels being dimensioned and configured to encircle the wearer and hold the breast supporting cups in place with the gel packs surrounding the women breast. The heat from each gel pack serves to reduce swelling and tenderness of the breast tissues during the premenstrual period, pregnancy or the post-pardem period.

A bra sport top provides enhanced posture and increased breast support for women engaging in athletic activities. Over-shoulder harness encircle each shoulder and serve to urge them back. Cross braces interconnect the two over-shoulder harnesses in a crosswise manner between the shoulder blades. A support belt traveling through a slip sleeve encircling the wearer's torso below the breast and shoulder blades. Interconnecting the over-shoulder harnesses and the slip sleeve are breast tensioning panels that compress and retrain the breast so as to prevent any damage to the breast tissue. The left and right breast-tensioning panels may be interconnected by a detachable coupling means or may be connected by elastic bands or the like. Alternative embodiments allow for different directional support of the underlying breast tissue by the breast-tensioning panels.

A breast presser belt comprising a belt body adapted to be removably wrapped around a breast portion of a user, a presser member adapted to extend from the belt body over the breast portion of the user, and a bag adapted to be inflated by means of appropriate fluid. The bag is attached to the inner surface of the presser member at a predetermined position. When the bag is inflated, the breast presser belt pressurizes the breast portion of a user and securely fastened to the breast portion. Thus, the pressurizing location of the breast presser belt is prevented from being shifted. The breast pressure belt does not require a user or patient to keep still on a bed. Allergic poisoning, previously experienced due to the use of medical adhesive tape may be obviated. The breast presser belt may be applied to a female having breast.

A two component post-operative compression garment for use in enhancing fluid drainage from a plurality of open micro-incisions in breasts after liposuction surgery has been performed on breasts. The compression garment includes a first garment component positionable on a person to cause a first magnitude of compression pressure upon the breasts, and a second garment component adjustably positionable in concert with the first garment component to cause an adjustable second magnitude of compression pressure greater than the first magnitude. This second magnitude of pressure is adjustable to thereby provide a pressure adequate to force fluid from the open micro-incisions of the breasts. Methodology of liposuction mammoplasty includes infiltrating each breast tumescently with a fluid that includes a local anesthetic. Thereafter, a plurality of micro-incisions are provided to the breast and fatty tissue is withdrawn suctionally with operating microcannulas inserted within the micro-incisions. Finally, the micro-cannulas are removed from the open micro-incisions and compression pressure is applied as with the above described compression garment to each breast for a period of time and of sufficient pressure to force the tumescent fluid from the breasts through the micro-incisions. Substantially identical liposuction methodology can be employed for abdominal areas.

A compression bandage according to the present invention includes an expandable band that overlaps a postoperative breast to support and provide secondary compression, and compression flaps each having first and second ends, the first ends being connected to the expandable band adjacent the area to be compressed and the second ends being securable. The compression flaps compress the post-operative breast when longitudinally extended, and maintain the compression when the second ends are fastened. The compression bandage further comprises a least one shoulder support or strap connected to the expandable band to reduce movement of the bandage. The compression bandage can also have a support belt attached to the expandable band for supporting the area to be compressed.

The invention refers to equipment for the generation of ultrasonic waves with regulation of the frequency and power range with two possibilities of working, in continuous or pulsating modes, to be transmitted by adequate means to the transducer. The invention discloses a supporting means such as a harness or similar. Said harness is directly applied on the breast with capacity to act on the same in a selective way by programming the amount of power to be transmitted to transducers in an individualized form. The invention permits the elimination of capsular contractures corresponding to degree IV in the scale.

While these units may be suitable for the particular purpose to which they address, they would not be as suitable for the purposes of the present invention as heretofore described.

It is therefore desirable to provide a breast compressing device able to using lateral breast compression to mechanically distort the implant into a stretched ovoid shape, in a controlled manner, thereby increasing its surface to volume ratio. It is further desirable to provide a breast compressing device which will stretch the periprosthetic scar tissue that is the potential source of Capsular Contracture. It is even further desirable to provide a breast compressing device able to significantly reduce the risk of developing spherical Capsular Contracture. It is still further desirable to provide a breast compressing device able to apply a compressive force of a range of magnitude (safe and therapeutically effective at the same time) determined through clinical studies with real patients in different stages of rehabilitation after surgery during manual self-compression. The Data Acquisition System used in these studies was specifically designed for the purpose of developing the breast compression device.

SUMMARY OF THE PRESENT INVENTION

The present invention relates generally to devices for compressing the breasts of a woman and, more specifically, to a device which is able to support a breast of a woman and provide a compression force in a controlled even manner on either side of the breast for relieving the effects of Capsular Contracture.

A primary object of the present invention is to provide a breast compressing device that will overcome the shortcomings of prior art devices.

Another object of the present invention is to provide a breast compressing device which is able to mechanically compress a breast of a woman and any implant within the breast in a controlled manner.

A further object of the present invention is to provide a breast compressing device which is able to be selectively used in the privacy of ones home.

A yet further object of the present invention is to provide a breast compressing device including an adjustable harness for securing the device about the body of the user and adjusted to fit various body sizes.

A still further object of the present invention is to provide a breast compressing device including an aperture for receiving the breast therein, supporting the breast and restricting movement of the breast.

Another object of the present invention is to provide a breast compressing device including horizontal and vertical adjustment elements for varying the size of the aperture.

An even further object of the present invention is to provide a breast compressing device having controllable opposing extendable and retratable compression elements and a pump for extending and retracting the opposing compression elements.

A yet further object of the present invention is to provide a breast a breast implant compression device having compression housing members which laterally extend upon application of a controllable pressure.

Another object of the present invention is to provide a breast a breast implant compression device wherein the compression housing members are connected by a common conduit to a source of air pressure.

An even further object of the present invention is to provide a breast implant compression device wherein the air pressure is applied to the compression elements by a hand held mechanical, electromechanical, or electronically controlled pump having a pressure gauge.

A still further object of the present invention is to provide a breast implant compression device able to increase breast implant surface area during compression cycles thereby stretching periprosthetic scar tissue, and therefore, preventing Capsular Contracture.

Another object of the present invention is to provide a breast compressing device that is simple and easy to use.

A yet further object of the present invention is to provide a breast compressing device that is economical in cost to manufacture.

Additional objects of the present invention will appear as the description proceeds. The breast compression device of the present invention provides numerous features and benefits. Some of the features and benefits are as follows:

Functional Features
1. The Breast Compressor Device applies a controlled, lateral compression equally to both sides of the breast to mechanically distort the implant into a stretched ovoid shape;
2. Operation of the Device is automatic, only requiring the user to turn it on;
3. The Device measures and monitors the applied pressure for proper control of the compression force delivered to the breast.

Performance Features
1. When activated, the device preferably applies a compression force for 10–20 seconds, followed by 5–10 seconds of relaxation. The compression time and relaxation time being adjustable and the preferred adjustable session time being 15 minutes for each breast;
2. The device is quiet and therefore not intrusive in a home environment;
3. The device operates for a minimum of 30 minutes without needing a battery recharge, battery recharge time being approximately 4 hours or less with a charger powered from 120 volts AC.

Physical Features
1. The breast compression device is lightweight and portable able to be worn comfortably by a post-surgical female patient following breast reconstruction or augmentation surgery;

2. The breast compression device is easy to put on and remove by a post-surgical patient whose strength and arm mobility may be limited for an indefinite period following surgery;
3. The breast compression device includes a strap mechanism or harness for supporting the weight of the device, holding the device firmly against the chest wall so that compression occurs at the base of the breast, and preventing shifting between compression cycles;
4. The compression members are able to prevent the breast implant from moving out of position while applying pressure to the breast;
5. The breast compression device includes an electronic control module and either rechargeable battery or AC transformer;
6. The breast compression device is adjustable to fit any size user;
7. The breast compression device includes Operating and Low Battery indicators;
8. The breast compression device includes a Power ON/OFF Switch; Pressure Set Switch allowing setting of maximum desired breast pressure by patient slowly until desired level of pressure is reached; a Session Start Switch for starting 15 minute sessions during which pressure is automatically increased until a desired level is reached, holding pressure for the required time, and then reliving; and a stop switch able to terminate the session and remove pressure from the breast which is selectively operated if patient feels pain Safety Features
1. The device exerts forces on the breast, which are less than the forces that may result in rupturing a breast implant. Redundant pressure monitoring and control means ensure that a single fault does not result in a hazard to the user. ASTM F703: Standard Specification for Implantable Breast Prostheses is used as control guidance with respect to acceptable forces to apply;
2. The breast compression device is safe to use at home by the patient;
3. The breast compression device terminates the session if the preset (not user-adjustable) maximum pressure limit is exceeded;
4. The breast compression device terminates the session upon activation of the stop switch by the patient;
5. The breast compression device contains Microprocessor Monitor (watchdog);
6. Low voltage system: AC transformer or rechargeable battery;
7. The breast compression device complies with FDA Design Control Requirements and Regulations; and
8. The breast compression device complies with domestic and international safety standards for electromechanical medical devices including, but not limited to. IEC 60601: Medical Electrical Equipment, General Requirements for Safety.

A device for compressing a breast. The device includes a harness able to be releasably secured to a body of a user and a compression member adjustably connected to the harness for receiving the breast of the user. A control module is releasably secured to the harness for providing a pressure to the compression member for applying an equal compression force to the breast. The compression member includes a first compressing element positioned on a first side of the breast; a second compression element positioned on a second side of the breast opposite the first compressing element; and a structural member extending between the first and second compressing elements for retaining the first and second compressing elements on respective sides of the breast whereby an aperture defined by the structural member and first and second compressing elements for receiving the breast therein. The harness includes a first strap for securing the device about a waist of the user and a shoulder strap adjustably connected to the first strap for retaining the compression member aligned with the breast of the user. The structural member includes a first length adjustable structural element extending between a first end of both the first and second compressing elements and a second length adjustable structural member extending between a second end of both the first and second compressing elements. The control element includes a pump and supply line connected between the pump and both the first and second compressing elements for providing air pressure thereto.

To the accomplishment of the above and related objects, this invention may be embodied in the form illustrated in the accompanying drawings, attention being called to the fact, however, that the drawings are illustrative only, and that changes may be made in the specific construction illustrated and described withing the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

DESCRIPTION OF THE REFERENCED NUMERALS

Figure 1:
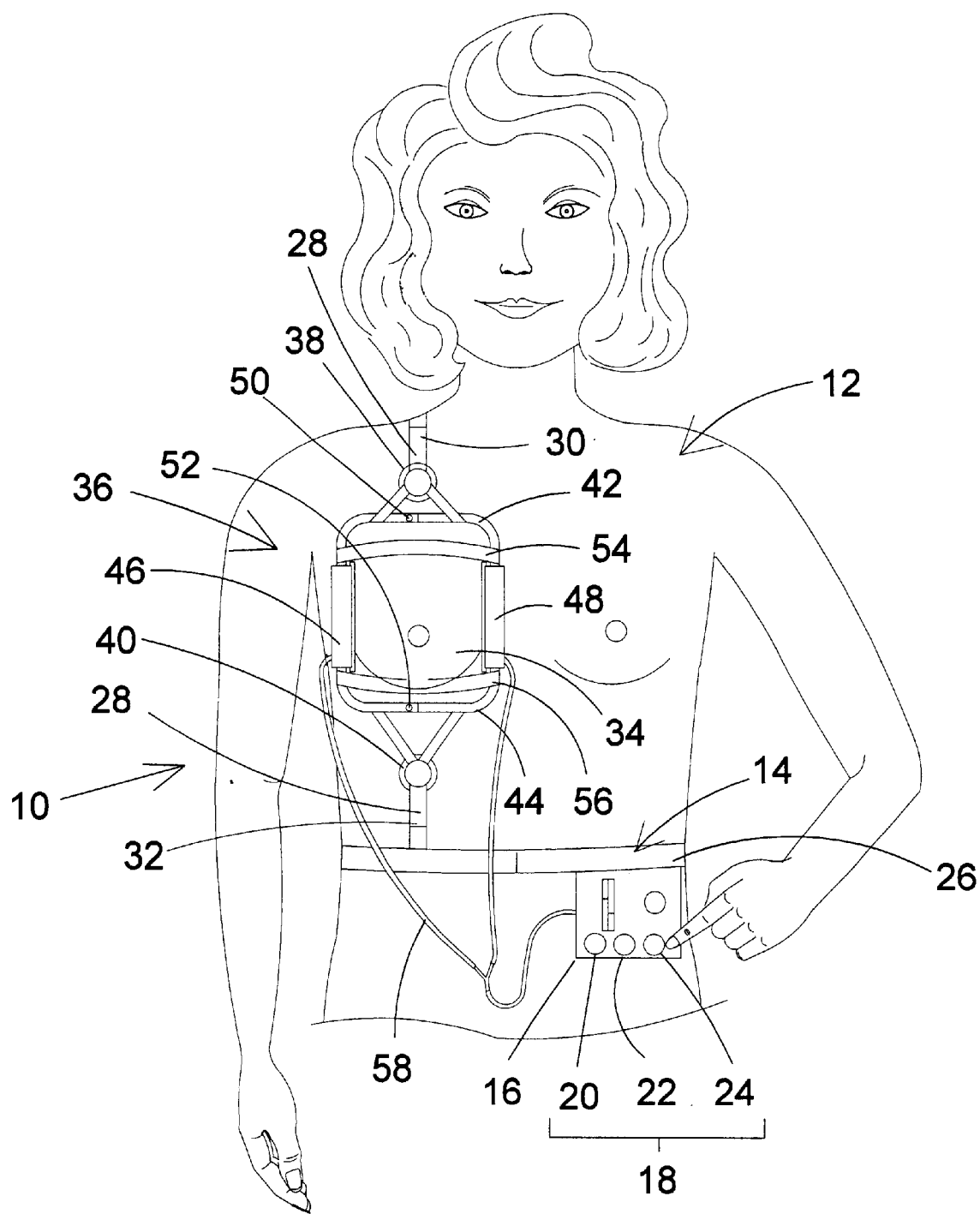
FIG. 1 is a front view of the breast compressing device of the present invention positioned on a body of a user.

Turning now descriptively to the drawings, in which similar reference characters denote similar elements throughout the several views, the Figures illustrate the breast compressing device of the present invention. With regard to the reference numerals used, the following numbering is used throughout the various drawing figures.

10 breast compressing device of the present invention
12 user 14 harness
16 electronic control module
18 control keys
20 key for selecting pressure to be applied
22 key for selecting the number of compressions per minute
24 key for selecting the duration of a session
26 waist strap
28 shoulder strap
30 first section of the shoulder strap
32 second section of the shoulder strap
43 breast
36 compression element
38 first loop
40 second loop
42 upper structural member
44 lower structural member
46 first compressor
48 second compressor
50 upper position retaining member
52 lower position retaining member
54 upper slidably adjustable elastic strap
56 lower slidably adjustable elastic strap
58 supply pipe
60 fastener of waist strap
62 fastening element of first section of shoulder strap
64 arrows indicating extension and retraction of structural members
66 first section of structural member
68 second section of structural member
70 recess in first section
72 microprocessor of electronic control module
74 power supply of electronic control module
76 air pump
78 first compression sensor
80 second compression sensor
82 air pressure source
84 first compression piston
86 first set of springs
88 first resilient mechanism
90 second resilient mechanism
92 second set of springs
94 second compression piston

DETAILED DESCRIPTION OF THE PREFERRED EMBODIMENT

Turning now descriptively to the drawings, in which similar reference characters denote similar elements throughout the several views, FIGS. 1 through 9 illustrate the breast compressing device of the present invention indicated generally by the numeral 10.

The breast compression device 10 of the present invention is intended for therapeutic treatment of postoperative female patients that have recently undergone breast augmentation or breast reconstruction following Mastectomy surgical procedures. The breast compressing device 10 is shown in FIG. 1 releasably secured to the torso of a user 12. The breast compressing device 10 includes a harness 14 and an electronic control module 16 positioned on the harness 14. The electronic control module 16 has control keys 18. The control keys 18 include a key 20 for selecting pressure to be applied (pounds per square inch) to a breast, a key 22 for selecting the number of compressions per minute (repetitions) and a key 24 for selecting the duration of a session (time) during which the breast is compressed. The control keys 18 allow the user to select settings for a motorized air pump incorporated within the electronic control module 16. The electronic control module 16 also includes electronic circuitry for terminating the session should the electronic control module remote air pressure sensors, located within the breast compression elements, detect a problem as will be discussed hereinafter.

The harness 14 includes a waist strap 26 and an adjustable shoulder strap 28. The adjustable shoulder strap 28 includes a first section 30 and a second section 32. The first section extends from the waist strap 26 along the back and over the shoulder of the user 12. The second section extends from the waist strap 26 partially along the midsection of the user 12 to a position slightly below the breast 34. Adjustably connected to an end of the first section opposite the connection of the first section 30 and the waist strap 26 is the compression element 36. The second section 32 is connected to an opposing side of the compression element 36 at an end opposite the connection of the second section 32 and the waist strap 26. The first section 30 includes a hook and loop fastener 38 for adjusting the length thereof. The second section 32 also includes a hook and loop fastener 38 for adjusting the length thereof. The lengths of the first and second sections 30 and 32, respectively, are adjusted so as to position the compression element 36 to receive the breast 34 of the user 12 therein. The position of the compression element 36 is adjusted based upon the size of the user 12 and such that the breast 34 of the user 12 is comfortably and securely positioned therein. The harness 14 is able to support the weight of the compression member 36 and hold the compression member 36 firmly against the chest wall so that compression occurs at the base of the breast thereby preventing the compression member 36 from shifting between compression cycles.

A first loop 38 is positioned on a first side of the compression element 36 for receiving the first section 30 of the shoulder strap 28 and a second loop 40 is positioned on a second side of the compression element 36 for receiving the second section 32 of the shoulder strap 28. The first loop 38 is connected to an upper structural member 42 and the second loop 40 is connected to a lower structural member 44. Extending between the upper and lower structural members 42 and 44, respectively, are first and second compressors 46 and 48, respectively. The upper and lower structural members 42 and 44 can be telescopically adjusted so that the first and second compressors 46 and 48 fixedly engage the sides of the breast 34. An upper position retaining member 50 is provided to retain the upper structural member 42 at a desired length and a lower position retaining member 50 is provided to retain the upper structural member 42 at a desired length thereby securing the first and second compressors 46 and 48 in position at a desired distance from one another and on either side of the breast 34. Thus, the breast 34 is snugly held between the first and second compressors 46 and 48. Positioned on the upper structural member 42 is an upper slidably adjustable elastic strap 54 and positioned on the lower structural member 44 is a lower slidably adjustable elastic strap 56. The upper and lower straps 54 and 56, respectively, are moved to a position above and below the implant during use of the breast compressing device 10 to prevent dislocation of a breast implant during a compression session. Extending between the control module 16 and the first and second compressors 46 and 48 is a supply pipe 58. The supply pipe provides air from the air pump within the electronic control module 16 causing the first and second compressors 46 and 48 to compress and retract at an equal pressure and rate.

Figure 2:
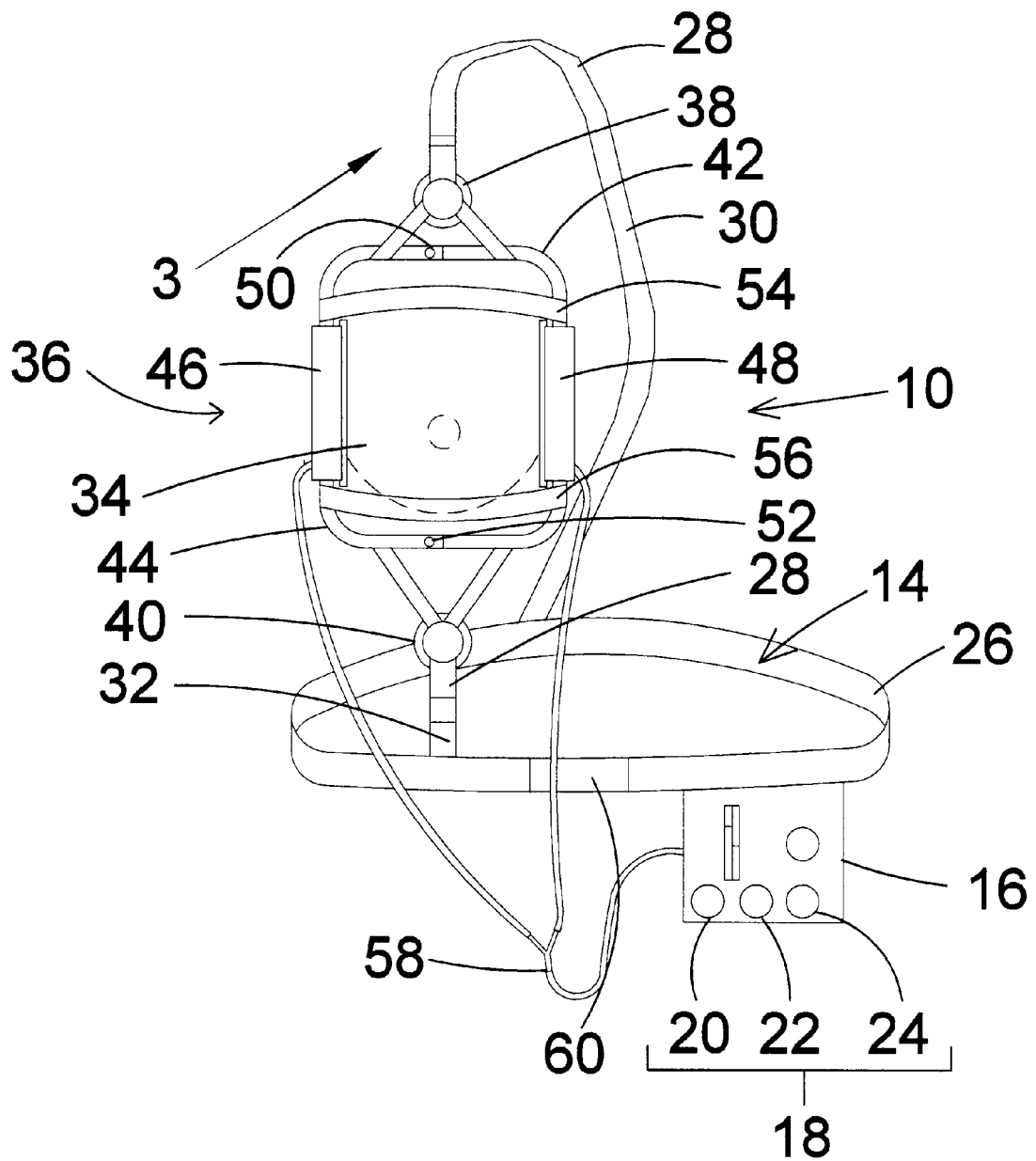
FIG. 2 is a front perspective view of the breast compressing device of the present invention.

A front view of the breast compressing device 10 is shown in FIG. 2. This figure illustrates the breast compressing device 10 in an unattached state with a breast 34 shown in dashed lines for reference purposes. As can be seen from this view, the waist strap 26 is able to extend entirely around the waist of a user. The breast compressing device 10 can be rotated to any position about the users body whereby the compression element 36 may receive either the left or right breast of the user. During use, once a compression session has been performed on one breast the user can readily rotate the compression element 36 to receive the other breast. The waist strap 26 includes a latch 60 for adjusting the size thereof to fit the user. The type of latch 60 shown in the figures is a hook and loop fastening device. However, any type of latch 60 able to secure the waist strap 26 about the waist of the user and also adjust the size of the waist strap 26 may be used. In order to secure the breast compressing device 10 about the body, the user releases the latch 60 and positions the waist strap 26 about the waist. The waist strap 26 is then secured about the waist of the user by securing the latch 60. The fastener of the first section 30 is then released and the first strap 30 is slipped over the shoulder of the user adjacent the breast 34 to be compressed. The length of the first strap 30 is then adjusted and the fastener fastened such that the desired breast 34 is positioned within the compression element 36. The upper and lower structural members 42 and 44 are then adjusted to position the first and second compressors 46 and 48, respectively, against respective sides of the breast 34 and the upper and lower position retaining members 50 and 52 secure the upper and lower structural members 42 and 44 in place. The upper and lower straps 54 and 56 are then positioned against the top and bottom of the breast 34, respectively, to retain the breast implant in the proper position prior to starting a session.

Figure 3:
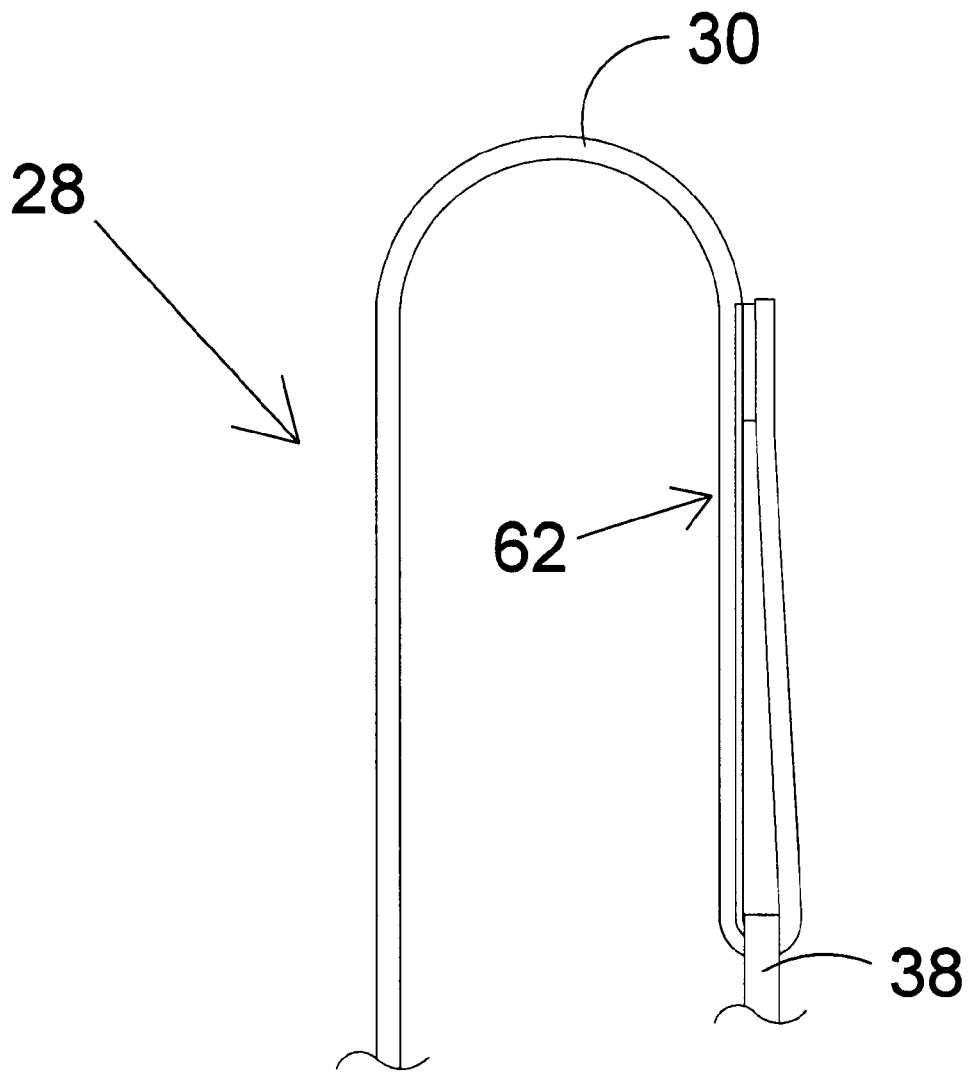
FIG. 3 is a side view of the shoulder strap of the breast compressing device of the present invention.

A side view of a portion of the first section 30 of the shoulder strap 28 is shown in FIG. 3. Because of the limited movement capability of the arm after surgery, the first section 30 of the shoulder strap 28 can be extended to form a large opening whereby the device can be slipped over the shoulder of the user without having to excessively raise the arm. Once the first section 30 of the shoulder strap 28 has been positioned on the shoulder the first section 30 is tightened by securing the fastening element 62. The fastening element 62 shown in the figure is a hook and loop fastening device. The end of the first section 30 extends through and loops around the first loop 38 for engaging the hook and loop fastener on the portion of the first section 30 not passing through the first loop 38. The second section 32 also includes a similar fastening device. The hook and loop fastener shown in the figures is for purposes of illustration only. For purposes of the present invention, any fastener able to adjustably secure the first section 30 to the compression element 36 may be used. Additionally, any fastener able to adjustably secure the second section 32 to the compression element 36 may be used.

Figure 4:
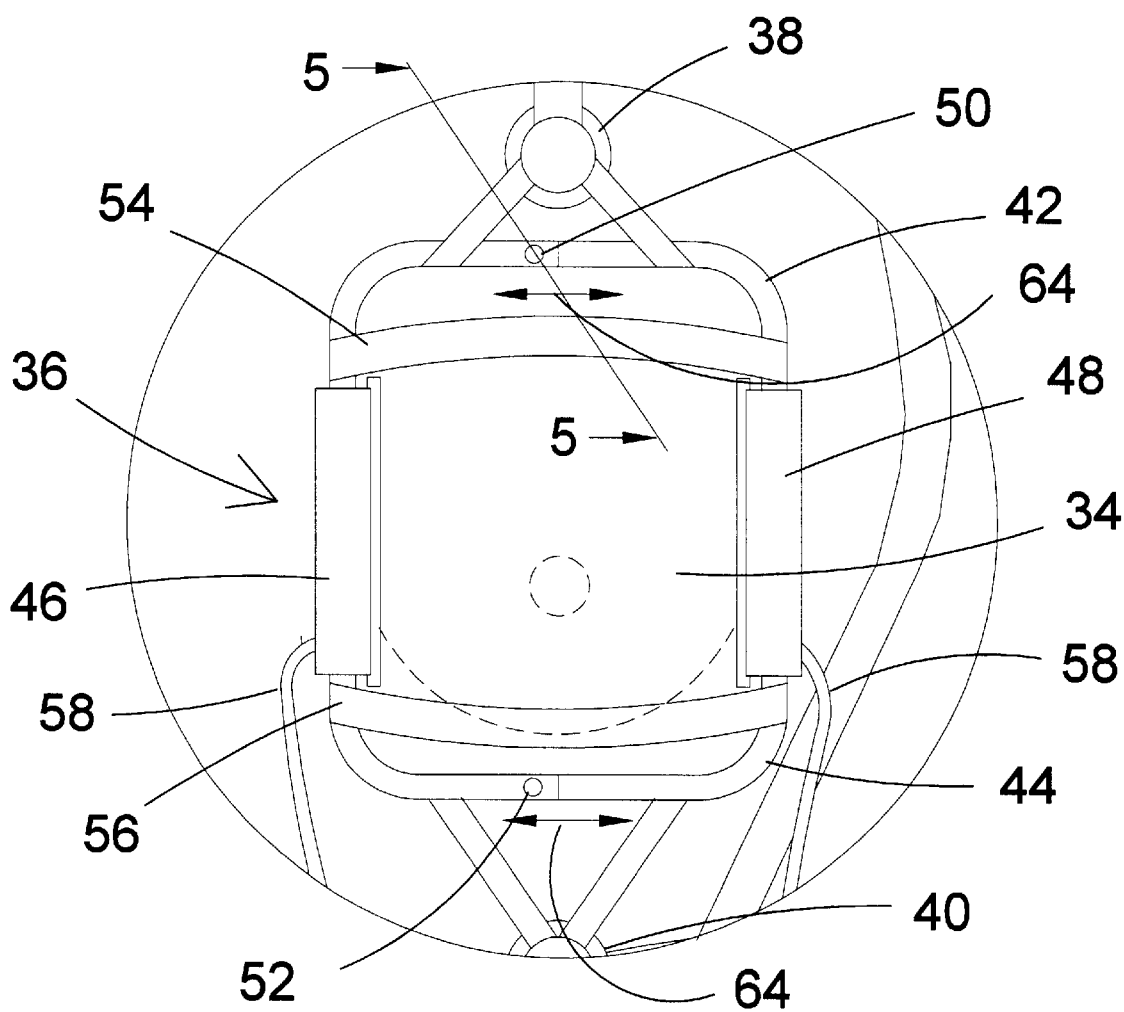
FIG. 4 is an enlarged view of the compression member of the breast compression device of the present invention.

An enlarged view of the compression element 36 of the present invention is shown in FIG. 4. As can be seen from this figure, the compression element 36 includes the first loop 38 on the first side thereof for receiving the first section 30 of the shoulder strap 28 and the second loop 40 for receiving the second section 32 of the shoulder strap 28 on a second side thereof opposite the first loop 38. The first loop 38 is connected to the upper structural member 42 and the second loop 40 is connected to the lower structural member 44. Extending between the upper and lower structural members 42 and 44, respectively, are the first and second compressors 46 and 48, respectively. The upper and lower structural members 42 and 44 can be telescopically adjusted to laterally adjust the first and second compressors 46 and 48 whereby the user can position the first and second compressors 46 and 48 at a predetermined optimal position contacting the sides of the breast 34. Extension and retraction of the upper and lower structural members 42 and 44, respectively, are indicated by the arrows labeled with the numeral 64. The upper position retaining member 50 is provided to retain the upper structural member 42 at a desired length and the lower position retaining member 50 is provided to retain the lower structural member 44 at a desired length thereby securing the first and second compressors 46 and 48 in position at a desired distance from one another and on either side of the breast 34. Thus, the breast 34 is snugly held between the first and second compressors 46 and 48. The upper slidably adjustable elastic strap 54 is positioned on the upper structural member 42 and the lower slidably adjustable elastic strap 56 is positioned on the lower structural member 44. The upper and lower straps 54 and 56, respectively, are moved to a position above and below the implant during use of the breast compressing device 10 to prevent dislocation of a breast implant during a compression session. The supply pipe extends between the control module 16 and both the first and second compressors 46 and 48 for providing air from the air pump within the electronic control module 16 to the first and second compressors 46 and 48 thereby compressing and retracting the first and second compressors 46 and 48 in a controlled maimer at an equal pressure and rate.

A frame is formed by the structural members and compressing elements of the compression member 36 which is able to resist the opposing compressive forces being applied to the breast. There are several ways to generate the requisite force, including, but not limited to pneumatic bladders, a double-ended screw mechanism, etc. Regardless of the mechanical origin of the compressive force, however, it will be applied equally to opposite sides of the breast through semi-rigid elements. In the case of compressive forces generated by pneumatic bladders, the compression member 36 includes a housing having semi-rigid elements which are laterally movable by air pressure and return to a seated position within the housing by means of a tensioning member once air pressure is released. At least one of the compression elements housings has a valve for connection of an air pressure source.

Figure 5:
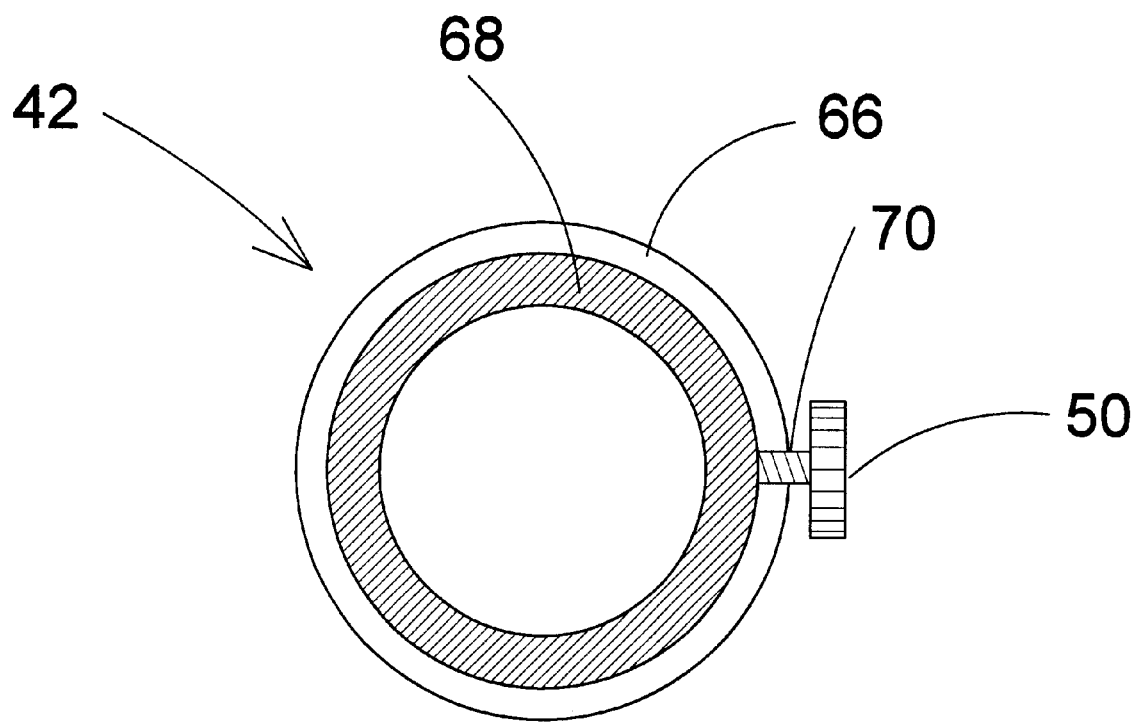
FIG. 5 is a cross sectional view of the lateral spacing adjustment members and fastening element of the breast compressing device of the present invention taken along the line 5—5 of FIG. 4.

A cross sectional view of the upper structural member 42 and upper position retaining member 50 taken along the line 5—5 of FIG. 4 is shown in FIG. 5. The lower structural member 44 and lower position retaining member 52 are similar in structure and thus will not be described herein. As can be seen from this figure, the upper structural member 42 includes a first section 66 and a second section 68. The first section 66 is cylindrical in shape and has an inner diameter which is substantially the same as the outer diameter of the second section 68. The second section 68 is slidably positioned to at least partially extend into the first section 66 and is moveable therein. A recess 70 extends through the first section 66. The upper position retaining member 50 extends through and releasably engages the recess 70. The upper position retaining member 50 extends through the recess and engages the outer side of the second section 68 to maintain the upper structural member 42 at a constant length. In order to increase or decrease the length of the upper structural member 42, the upper position retaining member 50 is at least partially removed from the recess 70 thereby disengaging the upper position retaining member 50 from its contact with the second section 68. At this point, the first and second sections 66 and 68 may be moved such that the second section 68 is inserted further into the first section 66 or removed therefrom until the desired length for the upper structural member 42 is obtained. At this point, the upper position retaining member 50 is inserted back into the recess so as to contact and engage the second section 68.

Figure 9:
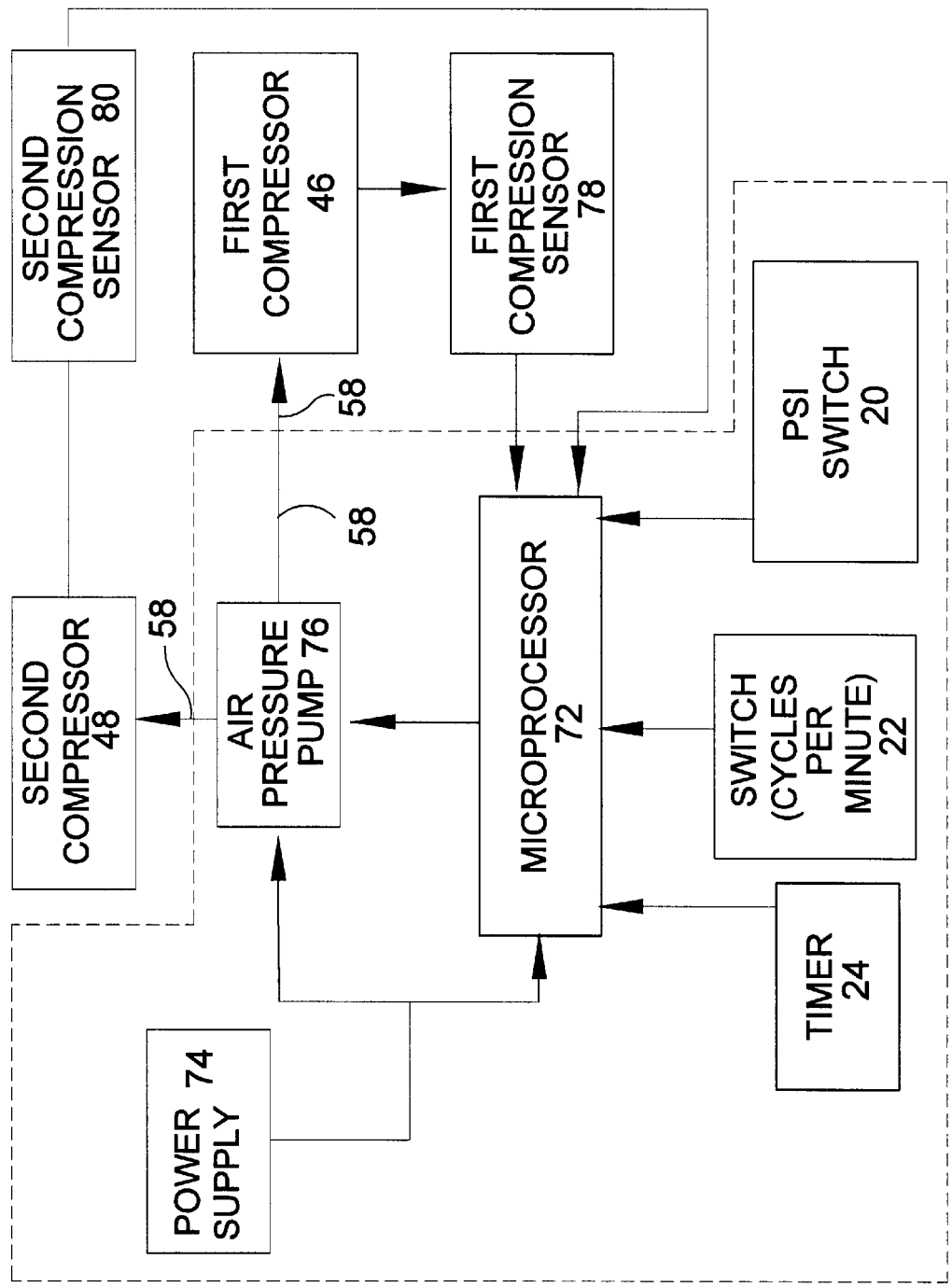
FIG. 9 is a block diagram of the breast compressing device of the present invention.

A block diagram illustrating the components of breast compressing device 10 is shown in FIG. 9. As can be seen from this figure, the electronic control module 16 includes a microprocessor 72 for controlling the operation of the breast compressing device 10. A power supply is connected to the microprocessor 72 for supplying power to the electronic control module 16. The key 20 for selecting pressure to be applied (pounds per square inch) to a breast, the key 22 for selecting the number of compressions per minute (repetitions) and the key 24 for setting the duration of a compression session are all connected to the microprocessor 72 for setting operating values within which the breast compressing device 10 will operate. An air pressure pump 76 is connected to both the microprocessor 72 and the power source 74. The microprocessor controls operation of the air pump 76 and the power supply 74 provides operating power for the air pump 76. The air pump 76 is connected to both the first and second compressors 46 and 48, respectively, through the supply pipe 58. Under control of the microprocessor 72, the air pump 76 is controlled to provide air through the supply pipe 58 to both the first and second compressors 46 and 48 causing the first and second compressors 46 and 48 to compress and retract. A first compression sensor 78 is connected to measure the pressure applied by the first compressor 46 and is connected to the microprocessor 72 for terminating control of the air pump 76 upon sensing the pressure applied by the first compressor 46 is above a preset limit set by the user with the key 22 for selecting the number of compressions per minute (repetitions). A second compression sensor 80 is connected to measure the pressure applied by the second compressor 48 and is connected to the microprocessor 72 for terminating control of the air pump 76 upon sensing the pressure applied by the second compressor 48 is above a preset limit set by the user with the key 22 for selecting the number of compressions per minute (repetitions). The microprocessor 72 controls the air pump 76 to expand and contract based upon the cycle time set by the key 22 for selecting the number of compressions per minute (repetitions) and also continues to control the air pump 76 for a time period set by the user with the key 24 for setting the duration of a compression session.

Figure 6:
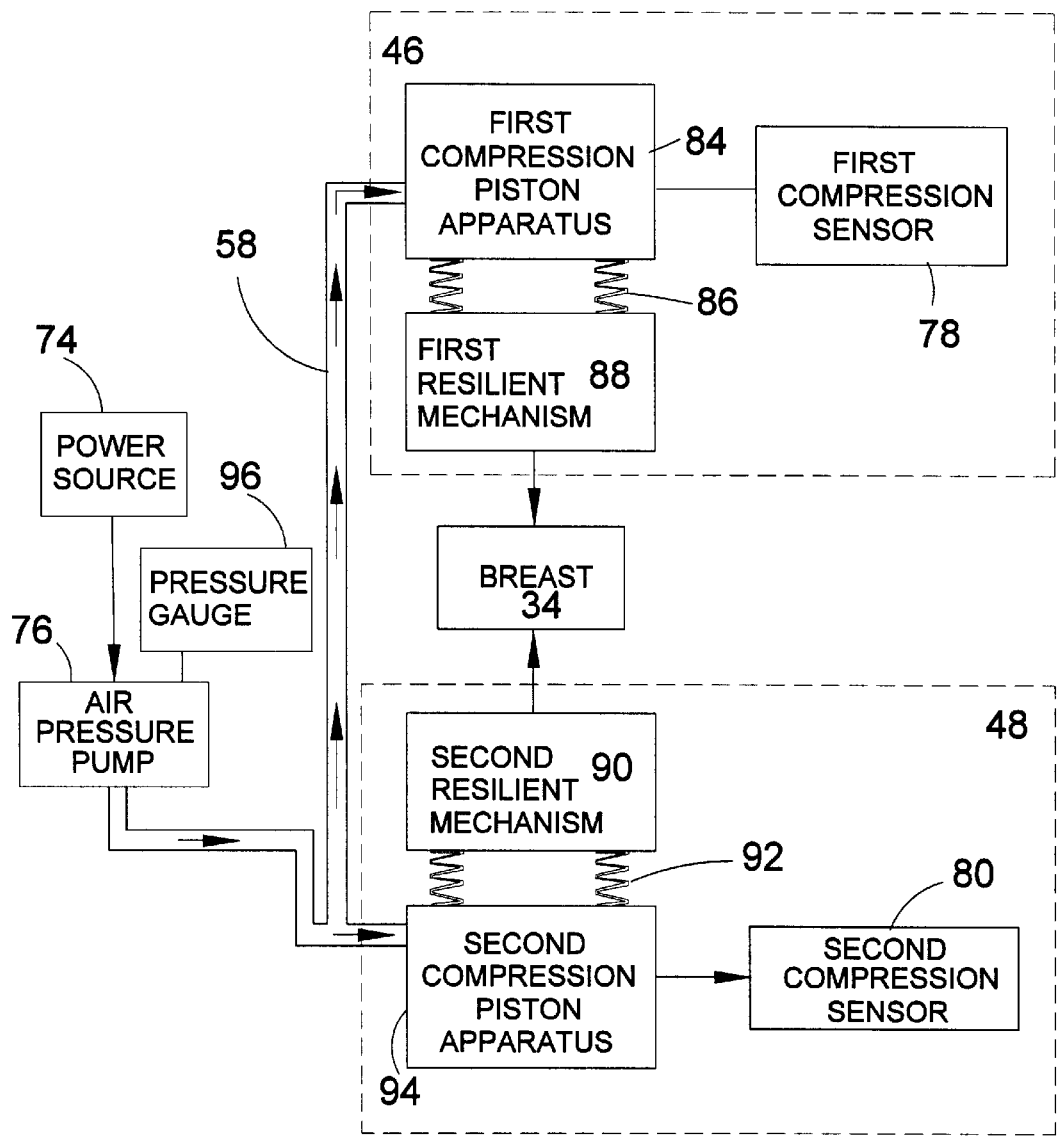
FIG. 6 is a block diagram of the battery operated air pressure operation of the breast compressing device of the present invention and showing the flow of air through the device.
Figure 7:
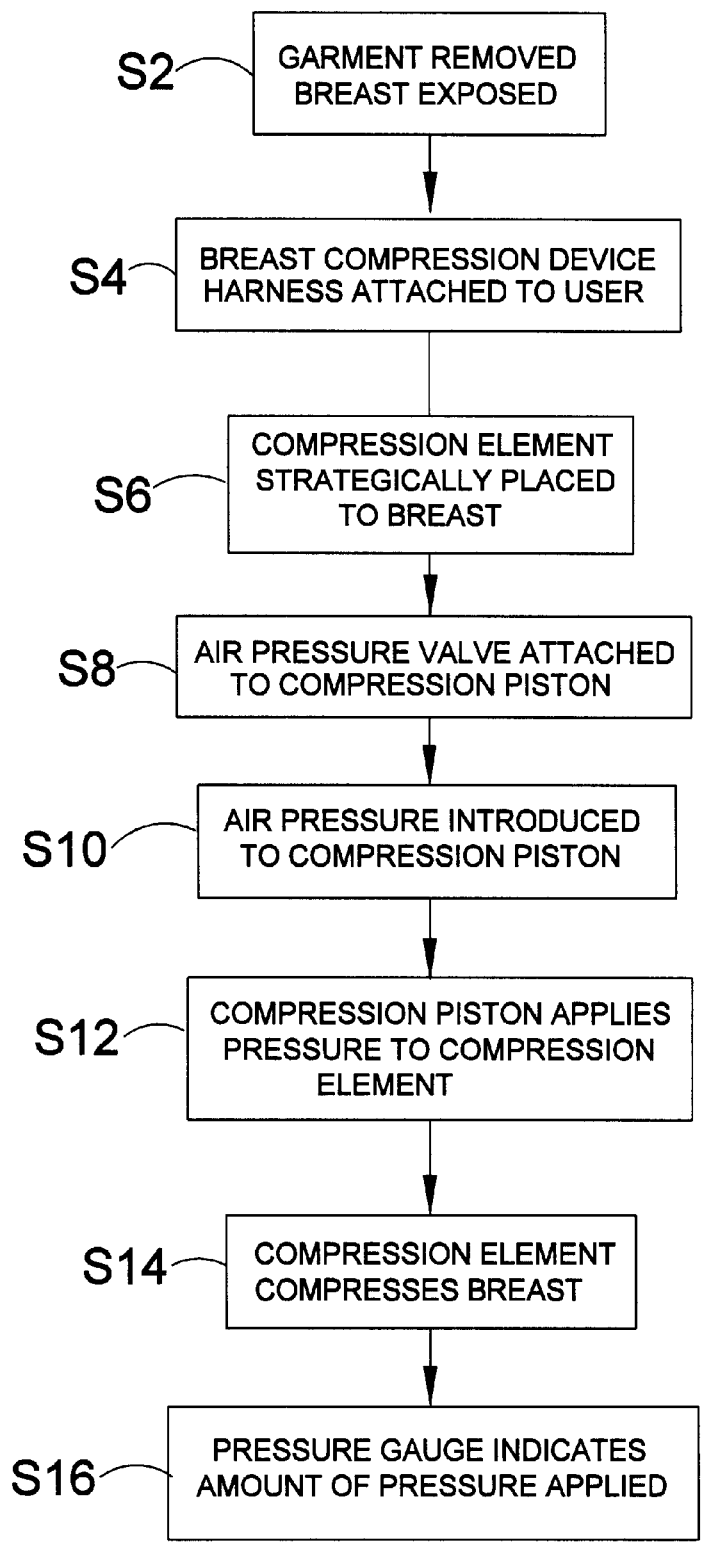
FIG. 7 is a flow diagram describing the mounting procedure for the breast compressing device of the present invention.

The operation of the breast compressing device 10 will now be described with reference to the figures and specifically FIGS. 6, 7 and 8. In operation, the breast compressing device 10 is releasably secured to a user as described in FIG. 7. As can be seen from this figure, the user 12 must first remove their garment and expose the breast 34 to be compressed as discussed in step S2. The breast compression device 10 is then secured to the body of the user 12 as stated in step S4. This is accomplished by releasing the latch 60 on the waist strap 26 and positioning the waist strap 26 about the waist. The waist strap 26 is then secured about the waist of the user 12 by securing the latch 60. The fastener of the first section 30 is then released and the first strap 30 is slipped over the shoulder of the user 12 adjacent the breast 34 to be compressed. The length of the first strap 30 is then adjusted and the fastener fastened such that the desired breast 34 is positioned at least partially within the aperture of the compression element 36 as described in step S6. In order to properly position the breast 34, the compression element 36 is positioned so that the breast 34 to be compressed is aligned with the aperture. The length of the upper and lower structural members 42 and 44 are adjusted to position the first and second compressors 46 and 48, respectively, against respective sides of the breast 34 and the upper and lower position retaining members 50 and 52 are engaged to maintain the length of the upper and lower structural members 42 and 44 constant. The upper and lower straps 54 and 56 are then positioned against the top and bottom of the breast 34, respectively, to retain the breast implant in the proper position prior to starting a compression session. At this time, the air pressure valve for measuring the air pressure supplied to the first and second compressors 46 and 48 is connected to the compression piston of the air pump 76 as discussed in step S8 and the breast compressing device 10 is ready for operation.

The compression and expansion of the first and second compressors 46 and 48 will now be described with specific reference to FIGS. 6 and 7. Upon setting the pressure limits, cycle time and session time, the microprocessor 72 controls the air pump 76 to introduce air into the first compression piston 84 located in the first compressor 46 and to the second compression piston 94 in the second compressor 48 as stated in step S10 via the supply pipe 58. The first air compression piston 84 in turn exerts a pressure on a first resilient mechanism 88 via a spring assembly 86 and the second air compression piston 94 in turn exerts a pressure on a second resilient mechanism 90 via a spring assembly 92 as stated in step S14. In response, the first and second resilient mechanisms 88 and 94 are caused to exert a force on their respective side of the breast 34. This causes the breast and breast implant to be compressed as discussed in step S14. The pressure applied to the breast 34 causes the implant to increase in surface area from a substantially spherical shape to an oval shape. The amount of pressure applied is indicated on the pressure gauge 96 as described in step S16. The first and second compression sensors 78 and 80 monitor the pressure of the first and second compression pistons 84 and 94, respectively. If the sensed pressure is greater than the pressure set by the user, the compression sensors transmit a control signal to the microprocessor 72 causing the microprocessor 72 to terminate the compression session. After pressure has been applied for the time period set by the user, the pressure applied by the first and second compression pistons 84 and 94 on the first and second resilient mechanisms 88 and 90 respectively is removed. This causes the first and second resilient mechanisms 88 and 90 to retract and remove the pressure applied to the breast. This pattern will repeat for the entire session period as set by the user.

Figure 8:
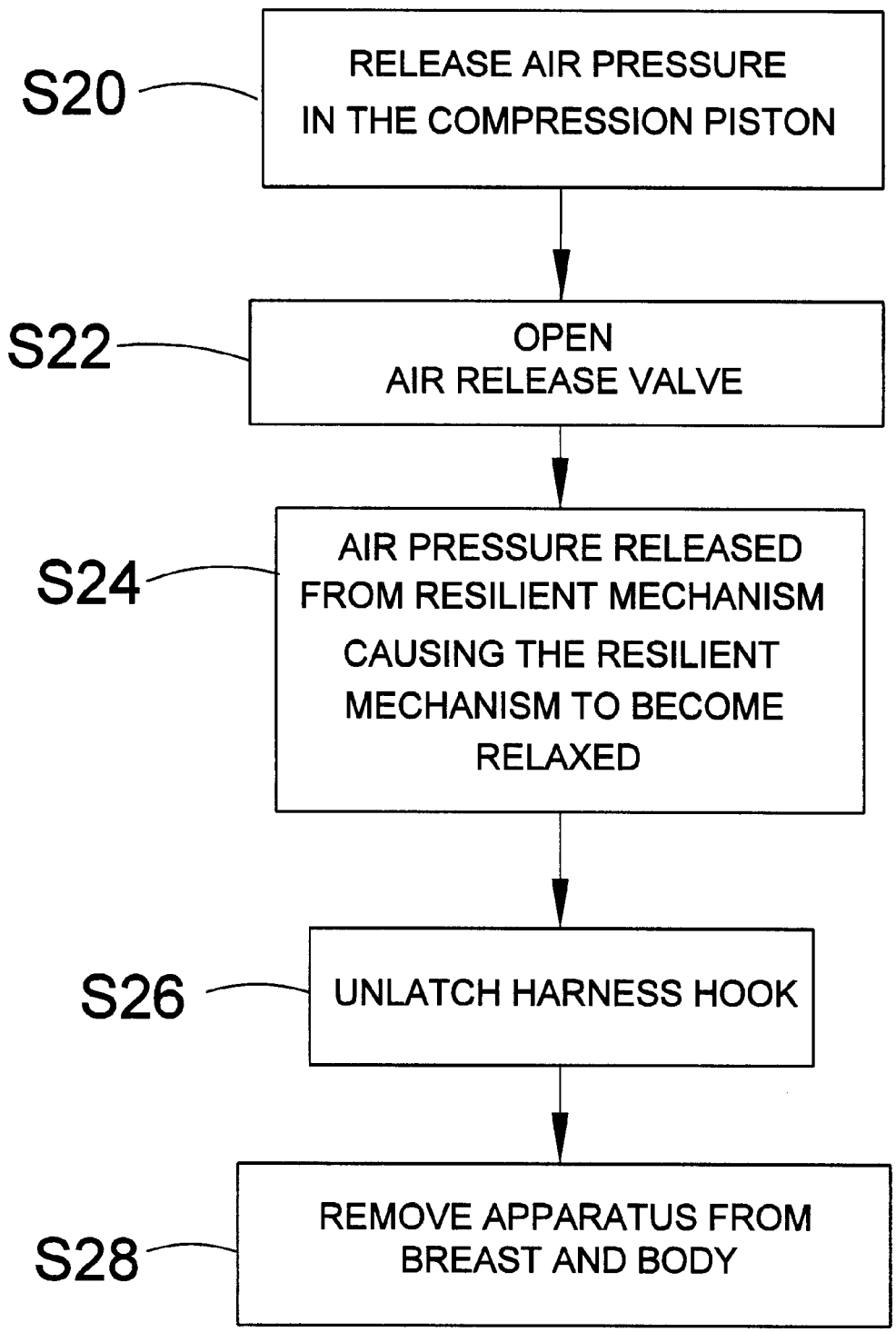
FIG. 8 is a flow diagram describing a procedure for dismounting of the breast compressing device of the present invention.

Upon completing the session, the breast compressing device 10 is removed from its position as described in FIG. 8. When the compression session is completed, the air pressure within the first and second compression pistons 84 and 94, respectively, is released as discussed in step S20. Then the air release valve on the piston is opened as stated in step S22. The air pressure is now released from the first and second resilient mechanisms 88 and 90 causing the first and second resilient mechanisms 88 and 90 to become relaxed as described in step S24. At this point the user unlatches the harness 14 by unfastening the fastener 60 of the waist strap 26 and the fastener 62 of the first section 30 of the shoulder strap 28 as discussed in step S26. The breast compressing device 10 is now able to be removed from the body of the user as stated in step S28. Once removed, the breast compressing device 10 may be positioned to compress the other breast in the manner described above or may be stored away until the next time use is desired.

The compression elements have a common conduit whereby when air pressure is introduced, the first and second compressing elements move in tandem. The pressure source can be mechanical, electromechanical, or an electronic device having means for increasing and decreasing air pressure and having a pressure gauge whereby the user can monitor the pressure. To achieve full therapeutic benefit of compression therapy, patients need to use the device up to several times per day starting as soon as one week after surgery (unless otherwise recommended by health-care professional). The session should last approximately 15 minutes for each breast with compression applied for ten seconds followed by ten seconds of relief. Since most Capsular Contracture problems tend to occur within the first six months following surgery, the breast compression device 10 should be used regularly during that interval, at least two times a day and electively one time a day after six months up to a year. Each implant patient that is judged to be an appropriate candidate for self use of the device receives specific instructions from a health-care professional on how to correctly use the new Device to best achieve the desired medical benefit.

From the above description it can be seen that the breast compressing device of the present invention is able to overcome the shortcomings of prior art devices by providing a breast compressing device which is able to mechanically compress a breast of a woman and any implant within the breast in a controlled manner. The breast compressing device includes an adjustable harness for securing the device about the body of the user and adjusted to fit various body sizes, an aperture for receiving the breast therein, supporting the breast and restricting movement of the breast and horizontal and vertical adjustment elements on opposing side of the aperture for varying the size of the aperture. The breast compressing device also includes a pair of controllable extendable and retractable compression elements positioned on opposite sides of the aperture for compressing the breast implant and a pump connected to the compression apertures via a conduit for extending and retracting the opposing compression elements. The breast implant compression device able to increase breast implant surface area during compression cycles thereby stretching and continuously contracting periprosthetic scar tissue. Furthermore, the breast compressing device of the present invention is simple and easy to use and economical in cost to manufacture.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A device for compressing a breast of a user, said device comprising:
   a) a harness able to be releasably secured to a body of the user;
   b) a compression member adjustably connected to said harness for receiving the breast of the user, said compression member including
      i) a first compressing element positioned on a first side of the breast;
      ii) a second compression element positioned on a second side of the breast opposite said first compressing element;
      iii) means extending between said first and second compressing elements for retaining said first and second compressing elements on respective sides of the breast whereby an aperture defined by said retaining means and first and second compressing elements for receiving the breast therein; and
   c) means for providing a pressure to said first and second compressing elements causing said first and second compressing elements to apply an equal compression force to the breast, wherein said retaining means includes a first structural member extending between a first end of said first compressing element and a first end of said second compressing element and a second structural member extending between a second end of said first compressing element and a second end of said second compressing element and said first and second structural members each have an adjustable length for adjusting a size of said aperture to a size of the breast of the user.

2. The breast compressing device as recited in claim 1, wherein said providing means is a control module including a pump and said device further includes a supply line connected between said pump and both said first and second compressing elements for providing air pressure therethrough.

3. The breast compressing device as recited in claim 2, wherein said control module is releasably connected to said harness and includes means for adjusting an amount of pressure provided by said pump to said first and second compressing elements.

4. The breast compressing device as recited in claim 3, wherein said pump controls compression and contraction of said first and second compressing elements.

5. The breast compressing device as recited in claim 4, wherein said control module further includes means for adjusting a time period during which pressure is supplied by said pump.

6. The breast compressing device as recited in claim 4, wherein said control module further includes means for adjusting a time period during which said first and second compressing elements expand and contract.

7. The breast compressing device as recited in claim 6, further comprising means for sensing an amount of pressure applied by said first and second compressing elements and causing said control module to terminate contraction of said first and second compressing elements upon sensing a pressure above a predetermined amount.

8. The device as recited in claim 1, wherein said harness includes a first strap for securing said device about a waist of the user and a shoulder strap adjustably connected to said first strap for retaining said compression member aligned with the breast of the user and said first strap is length adjustable.

9. The device as recited in claim 4, wherein said harness includes a first strap for securing said device about a waist of the user and a shoulder strap adjustably connected to said first strap for retaining said compression member aligned with the breast of the user and said shoulder strap is length adjustable to thereby adjust the position of said compression member.

10. The breast compression device as recited in claim 2, wherein said pump is one of a mechanical, electro-mechanical, and eletronically controlled pump.

11. The breast compression device as recited in claim 10, further comprising a pressure gauge for providing a visual indication of the pressure provided by said pump.

12. A device for compressing a breast of a user, said device comprising:
- a) a harness able to be releasably secured to a body of the user;
- b) a compression member adjustably connected to said harness for receiving the breast of the user, said compression member including
    - i) a first compressing element positioned on a first side of the breast;
    - ii) a second compression element positioned on a second side of the breast opposite said first compressing element;
    - iii) means extending between said first and second compressing elements for retaining said first and second compressing elements on respective sides of the breast whereby an aperture defined by said retaining means and first and second compressing elements for receiving the breast therein; and
- c) means for providing a pressure to said first and second compressing elements causing said first and second compressing elements to apply an equal compression force to the breast, wherein said retaining means includes a first structural member extending between a first end of said first compressing element and a first end of said second compressing element and a second structural member extending between a second end of said first compressing element and a second end of said second compressing element; and further comprising
- d) first and second straps extending parallel to said first and second structural members and slidable thereon for contacting a top and bottom side of the breast respectively thereby securing the breast in position within said aperture.

* * * * *